United States Patent [19]

Ghaussy

[11] 4,392,497
[45] Jul. 12, 1983

[54] ERYTHROCYTE SEDIMENTATION RATE APPARATUS AND METHOD

[76] Inventor: Rahmat U. Ghaussy, 15300 W. Nine Mile Rd., Southfield, Mich. 48075

[21] Appl. No.: 212,134

[22] Filed: Dec. 2, 1980

[51] Int. Cl.³ ............................................. G01N 33/48
[52] U.S. Cl. .................................... 128/637; 73/61.4; 128/764
[58] Field of Search ........................... 73/61.4, 864.52; 128/637, 764

[56] References Cited

U.S. PATENT DOCUMENTS

| | | | |
|---|---|---|---|
| 3,626,762 | 12/1971 | Gilford | 73/864.52 |
| 3,734,079 | 5/1973 | Weber | 73/61.4 |
| 3,890,203 | 6/1975 | Mehl | 128/764 |
| 4,278,437 | 7/1981 | Hagger | 128/764 |

Primary Examiner—S. Clement Swisher
Attorney, Agent, or Firm—McCormick, Paulding & Huber

[57] ABSTRACT

Erythrocyte Sedimentation Rate is determined by collecting a predetermined quantity of venous blood directly within a sealed evacuated ESR specimen tube which may contain a specific quantity of an anticoagulant, agitating the sealed specimen tube to mix thoroughly the anticoagulant with the blood, supporting the sealed specimen tube in a precise axially vertical position, and measuring the distance from the bottom of the surface meniscus to the top of the column of red cells at a predetermined time after the sealed specimen tube has been vertically positioned. The ESR specimen tube has a diametrically enlarged portion at one end fitted with a penetrable elastomeric sealing stopper and may be graduated along its length.

7 Claims, 3 Drawing Figures

U.S. Patent   Jul. 12, 1983   4,392,497
FIG. 1
FIG. 2
FIG. 3
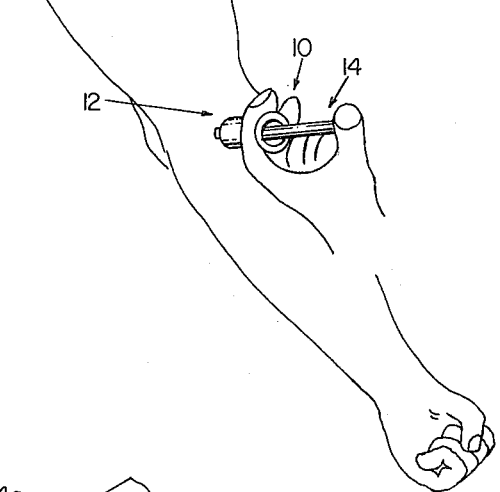
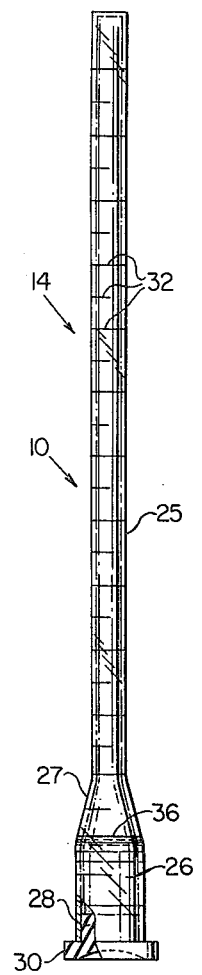
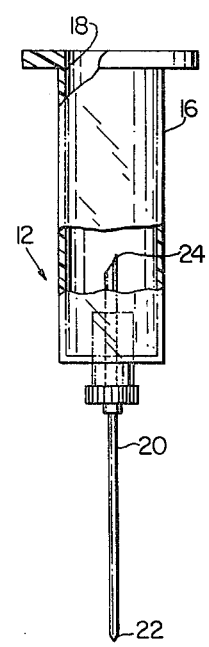
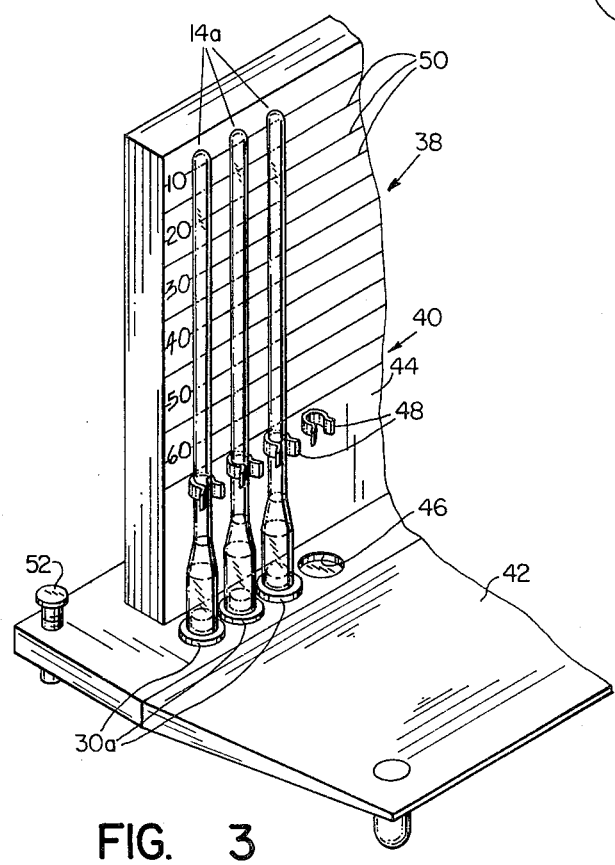

ERYTHROCYTE SEDIMENTATION RATE APPARATUS AND METHOD

BACKGROUND OF THE INVENTION

This invention relates in general to methods and apparatus for analytical analysis of blood and deals more particularly with an improved erythrocyte sedimentation rate apparatus and method. The erythrocyte sedimentation rate or ESR is the rate at which erythrocytes fall to the bottom of a column of anticoagulated blood and is used in the diagnosing progress of certain pathologic conditions, especially inflammatory disorders. In the performance of this test, it is usual to collect a venous blood specimen of somewhat greater quantity than required for the test. A predetermined quantity of whole blood is transferred from the specimen container to a graduated tube, using a graduated pipette, for example. Using another graduated pipette, a predetermined quantity of anticoagulant solution is added to the whole blood. When the blood and anticoagulant have been thoroughly mixed, the graduated tube containing the mixture is supported in axially vertical position. After a predetermined period of time, usually sixty minutes, the distance from the bottom of the surface meniscus to the top of the column of red cells is recorded in millimeters. The distance through which the erythrocytes fall during one hour measured in millimeters is the ESR value.

While presently accepted test methods generally yield satisfactory results, considerable time is required to perform these tests and several pieces of laboratory equipment are used. The transferring of blood from one container to another and the handling of open containers of blood during the test procedure exposes laboratory personnel to possible infectious disease, such as hepatitis, and also introduces the risk of blood specimen contamination and spillage. The present invention is concerned with these problems.

BRIEF DESCRIPTION OF THE DRAWINGS

FIG. 1 is a perspective view showing apparatus embodying the invention used to collect a blood specimen.

FIG. 2 is an exploded side elevational view of the apparatus shown in FIG. 1.

FIG. 3 is a fragmentary perspective view of other apparatus embodying the invention.

DETAILED DESCRIPTION OF PREFERRED METHODS AND EMBODIMENTS

Turning now to the drawing, an erthrocyte sedimentation rate (ESR) apparatus embodying the present invention is indicated generally by the reference numeral 10 in FIG. 1. The apparatus 10 comprises a direct flow sample needle assembly indicated generally at 12 and a sealed, evacuated ESR specimen tube designated generally by the numeral 14. The apparatus 10 is used both to collect a blood sample and to determine its ESR value, as will be hereinafter further discussed.

Considering the apparatus 10 in further detail, the direct flow needle assembly 12, best shown in FIG. 2, is of conventional type, includes a hollow tubular body 16, which is preferably made from transparent plastic or like material, and has a smooth cylindrical bore 18 which opens through its upper end, as it appears oriented in FIG. 2. An elongated hollow tubular needle 20, mounted in fixed position at the lower end of the body 16, has an axially elongated portion exposed externally of the body which terminates at a sharp end 22. The needle 20 extends coaxially into the bore 18 for some distance and has another sharp end 24 disposed within the bore, substantially as shown. The illustrated direct flow sample needle 12 is part of a VENOJECT Blood Collection System marketed by Kimble-Terumo, Inc., Elkton, Md. 21921. However, it should be understood that any suitable direct flow sample needle may be used in practicing the invention.

The illustrated ESR specimen tube 14 is preferably made from transparent plastic or laboratory glass, comprises an axially elongated generally cylindrical tube which is closed at its upper end, as it appears oriented in FIG. 2, and is 18 centimeters in overall length. The upper or main body portion of the tube, indicated at 25, is 14.8 centimeters in length and has a substantially uniform interior cross section, the diameter of which is 0.8 centimeters. A diametrically enlarged lower end portion, indicated at 26, is 1.9 centimeters in length and has a substantially uniform interior cross section, the diameter of which is 1.3 centimeters. An integral generally conically tapered transitional portion 27 provides connection between the upper and lower portions of the specimen tube 14. A penetrable elastomeric stopper 28, which seals the lower end of the tube 14, has a diametrically enlarged cylindrical flange 30 which extends outwardly beyond the periphery of the tube to adapt the tube 14 for use with the illustrated direct flow sample needle 12. The flange 30 has a diameter at least equal to the diameter of the bore 18 for effecting sealing engagement with the wall of the bore when the ESR specimen tube 14 is inserted into the body 16. The illustrated tube 14 is graduated or calibrated with indicia of linear measurement along its length. Although the space within the tube 14 is substantially evacuated, the tube may contain a predetermined quantity of anticoagulant solution, such as indicated at 36 in FIG. 2.

A blood specimen is collected in a conventional manner using the apparatus 10, as shown in FIG. 1. After the needle 20 has been inserted into a vein, the ESR specimen tube 14 is moved axially within the bore 18 and toward the needle end 24 to cause the latter needle end to penetrate and pass through the elastomeric stopper 28 into the sealed tube which, in turn, causes a blood specimen to flow into and substantially fill the evacuated portion of the tube. When the ESR tube 14 containing the blood specimen is withdrawn from the needle assembly 12, the hole formed in the resilient stopper 28 by the needle end 24 closes to effectively reseal the tube 14. The sealed specimen tube 14 which contains the blood specimen may now be transported by any convenient means to a laboratory for further testing.

Preparatory to determining the ESR value, the blood specimen and anticoagulant solution are thoroughly mixed. This mixing may be accomplished by inverting the ESR specimen tube 14 several times. The sealed ESR specimen tube 14 containing the anticoagulated blood sample is next supported in an axially vertical position with the stopper 28 at its lower end. The tube is maintained in its axially vertical position for a predetermined period of time. At the end of the predetermined period the distance from the bottom of the surface minescus to the top of the column of red cells is measured to determine the ESR value of the blood specimen. If the demarcation between the plasma and red cell columns should be hazy, the height of the red cell column is taken to be where full density is first apparent.

If, due to error, the ESR value is read at the wrong time, it is merely necessary to shake the ESR specimen tube until a homogeneous mixture is attained and repeat the test procedure.

The invention may be practiced with an ESR specimen tube which has a substantially uniform interior cross section throughout its entire length, however, the use of an ESR specimen tube, such as the bi-diameter tube 14, which has a relatively small uniform cross sectional area throughout a substantial portion of its length, facilitates accurate ESR value determination in a relatively short period of time. The reading time for the test may be varied. However, the ESR specimen tube will, of course, be calibrated to yield an ESR value in accordance with accepted standards.

Referring now to FIG. 3, another apparatus embodying the invention is illustrated and indicated generally by the reference numeral 38. The illustrated apparatus 38 includes a test rack designated generally by the numeral 40 and a plurality of sealed, evaluated ESR specimen tubes indicated generally at 14a, 14a and shown supported in axially vertically oriented test position on the rack 40. Three specimen tubes are shown, for convenience in illustrating the invention, however, the rack 40 may be constructed and arranged to accommodate any convenient number of specimen tubes. Each tube 14a is similar in most respects to the tube 14, previously described, however, it should be noted that the tubes 14a, 14a do not have graduations therealong.

The rack 40 has a base 42 which supports an upright panel member 44. A series of upwardly opening cylindrical apertures 46, 46 are formed in the base 42 for receiving the enlarged annular flanges 30a, 30a of the specimen tubes 14a, 14a. A plurality of spring clips 48, 48 are secured to the panel member 48, substantially as shown, each clip being in vertical alignment with an associated aperture 46. The panel 44 is calibrated with indicia of vertical linear measurement, as indicated at 50, 50. The graduations 50, 50 are calibrated to correspond to the physical dimensions of the tubes 14a, 14a. Adjustment screws 52 (one shown) are threadably engaged with the base 42 to facilitate leveling the rack 40 to support a plurality of specimen tubes 14a, 14a in precise axially vertical position.

In determining the ESR value of a blood specimen using the apparatus 38, a sealed ESR specimen tube 14a containing a mixture of blood and anticoagulant solution is clipped in axially vertical position on the rack 44 immediately after agitation. The specimen may be "zeroed" with respect to the leveled rack by vertically adjusting the specimen tube to horizontally align the meniscus of the blood column with the zero graduation on the panel 48. The associated aperture 46 which receives the flange 30a on the specimen tube is of sufficient depth to accommodate some vertical adjustment of the tube 14a relative to the rack. The associated spring clip 48 holds the specimen tube in its adjusted position relative to the rack 40. At the end of a predetermined period of time the distance from the bottom of the surface meniscus to the top of the column of red cells may be read with reference to the graduations 54, 54, with proper consideration for parallax, to determine the ESR value of the specimen. Using a bi-diameter ESR specimen tube, such as hereinbefore described, accurate test results are attained employing a one-half (½) hour test reading time.

I claim:

1. Erthrocyte sedimentation rate apparatus for use with a direct flow needle assembly having a hollow tubular body including a smooth cylindrical first bore opening through one end of the body, and an elongated hollow tubular needle mounted in fixed position at the other end of the body and extending through said other end and coaxially into said first bore, the needle having one sharp end exposed within said bore and another sharp end exposed externally of said body, said erythrocyte sedimentation rate apparatus comprising an axially elongated transparent generally cylindrical ESR specimen tube having a main body portion and a diametrically enlarged portion at one end, said tube having a generally cylindrical blind second bore opening through said one end, said main body portion having a uniform interior cross section throughout its length, a penetrable elastomeric stopper received within said one end and sealing said tube, said cylindrical stopper having an integral diametrically enlarged and generally cylindrical flange exposed externally of said tube and projecting beyond the periphery of said tube, said flange having a diameter substantially equal to the diameter of said first bore, the space within said tube being substantially evacuated, and rack means for supporting said ESR specimen tube in axially vertical position and having a horizontally disposed base and a panel supported on and extending vertically upwardly from said base, a clip mounted on said panel for engaging and releasably retaining said main body portion, and an upwardly opening generally cylindrical aperture in said base in axially vertical alignment with said clip, said aperture having a diameter substantially equal to the diameter of said cylindrical flange.

2. An erythrocyte sedimentation rate apparatus as set forth in claim 1 wherein said tube has indicia of linear measurement along its length.

3. An erythrocyte sedimentation rate apparatus as set forth in either claim 1 or claim 2 including a quantity of anticoagulant solution contained within said sealed evacuated tube.

4. An erythrocyte sedimentation rate apparatus as set forth in claim 1 wherein said tube includes an integral generally conically tapered transitional portion intermediate said main body portion and said diametrically enlarged portion.

5. An erythrocyte sedimentation rate apparatus as set forth in claim 1 wherein said panel has indicia of vertical linear measurement thereon.

6. Erythrocyte sedimentation rate apparatus for use with a direct flow needle assembly having a hollow tubular body including a smooth cylindrical first bore opening through one end of the body, and an elongated hollow tubular needle mounted in fixed position at the other end of the body and extending through said other end and coaxially into said first bore, the needle having one sharp end exposed within said bore and another sharp end exposed externally of said body, said erythrocyte sedimentation rate apparatus comprising an axially elongated transparent generally cylindrical ESP specimen tube having a main body portion and a diametrically enlarged portion at one end, said tube having a generally cylindrical blind second bore opening through said one end, said main body portion having a uniform interior cross section throughout its length, a penetrable elastomeric stopper received within said one end and sealing said tube, said cylindrical stopper having an integral diametrically enlarged and generally cylindrical flange exposed externally of said tube, said flange having a diameter substantially equal to the diameter of said first bore, the space within said tube being substantially evacuated, a rack having a horizontally disposed base and a generally vertically disposed portion, and holding means on said rack for engaging axially spaced apart portions of said ESR specimen tube to releasably retain said specimen tube in axially vertical portion.

7. An erythrocyte sedimentation rate apparatus as set forth in claim 6 wherein said vertically disposed portion comprises a panel having indicia of linear measurement thereon and said holding means comprises means for releasably retaining said specimen tube in a precise predetermined position relative to said rack.

* * * * *